United States Patent
Abe

(10) Patent No.: US 10,034,611 B2
(45) Date of Patent: Jul. 31, 2018

(54) SUBJECT INFORMATION OBTAINING APPARATUS AND SUBJECT INFORMATION OBTAINING METHOD

(75) Inventor: Hiroshi Abe, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 219 days.

(21) Appl. No.: 14/118,530

(22) PCT Filed: May 15, 2012

(86) PCT No.: PCT/JP2012/003165
§ 371 (c)(1),
(2), (4) Date: Nov. 18, 2013

(87) PCT Pub. No.: WO2012/160776
PCT Pub. Date: Nov. 29, 2012

(65) Prior Publication Data
US 2014/0114172 A1 Apr. 24, 2014

(30) Foreign Application Priority Data

May 20, 2011 (JP) .................. 2011-113908

(51) Int. Cl.
*A61B 5/00* (2006.01)
*A61B 8/14* (2006.01)

(52) U.S. Cl.
CPC .............. *A61B 5/0095* (2013.01); *A61B 5/72* (2013.01); *A61B 5/7203* (2013.01); *A61B 8/14* (2013.01)

(58) Field of Classification Search
CPC ....... A61B 5/00; A61B 5/0093; A61B 5/0095; A61B 5/72; A61B 5/7203
See application file for complete search history.

(56) References Cited

U.S. PATENT DOCUMENTS 4,598,589 A * 7/1986 Riley et al. .................... 73/609
2003/0225320 A1 12/2003 Jeon et al.
(Continued)

FOREIGN PATENT DOCUMENTS

WO 2010/074103 A1 7/2010

OTHER PUBLICATIONS

"Concomitant speed-of-sound tomography in photoacoustic imaging" by Manohar et al. Applied Physics Letters. 91, 131911 (2007) (hereinafter as Manohar et al).*

(Continued)

*Primary Examiner* — Tse Chen
*Assistant Examiner* — Jason Ip
(74) *Attorney, Agent, or Firm* — Canon U.S.A., Inc. IP Division

(57) ABSTRACT

A subject information obtaining apparatus and a subject information obtaining method are provided with which a resolution of a photoacoustic image can be improved even when an absorber arranged at a particular position with respect to a detector for photoacoustic waves is used.
The subject information obtaining apparatus is configured to obtain an optical characteristic value distribution of a subject by using photoacoustic waves. A signal processing apparatus constituting this subject information obtaining apparatus executes generating a correction table on the basis of a variation quantity of a signal intensity related to a signal from an ultrasonic wave detector and processing a signal from a photoacoustic wave detector by using a value of the correction table.

15 Claims, 11 Drawing Sheets

(56) References Cited

U.S. PATENT DOCUMENTS

| | | | |
|---|---|---|---|
| 2009/0066949 A1* | 3/2009 | Masumura | 356/326 |
| 2010/0041987 A1* | 2/2010 | Manohar | A61B 5/0095 |
| | | | 600/437 |
| 2010/0049044 A1* | 2/2010 | Burcher | 600/437 |
| 2010/0094561 A1 | 4/2010 | Masumura | |
| 2011/0106478 A1 | 5/2011 | Someda | |

OTHER PUBLICATIONS

"Correction of the effects of acoustic heterogeneity on thermoacoustic tomography using transmission ultrasound tomography" by X. Jin et al. Photons Plus Ultrasound: Imaging and Sensing 2006. Proceedings of SPIE. vol. 6086. pp. 1-5. 2006.*

C.-K. Liao, M.-L. Li, P.-C. Li, Optoacoustic Imaging with Synthetic Aperture Focusing and Coherence Weighting, Optics Letters, Nov. 1, 2004, 29(21):2506-2508, The Optical Society of America, Washington, DC, USA, 2004.

* cited by examiner

[Fig. 1]
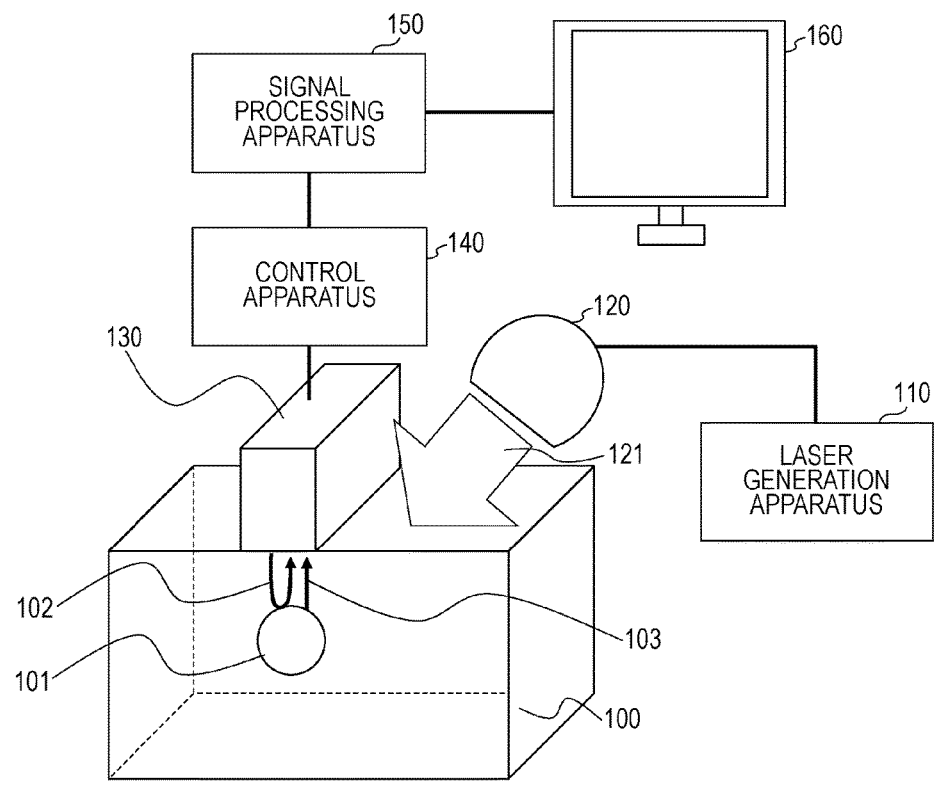

[Fig. 2]
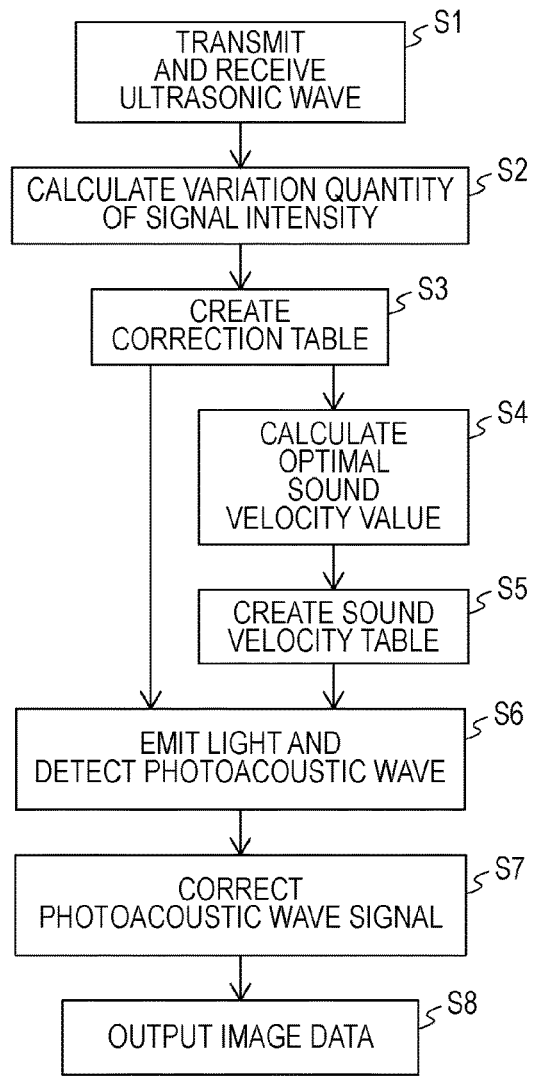
[Fig. 3A]
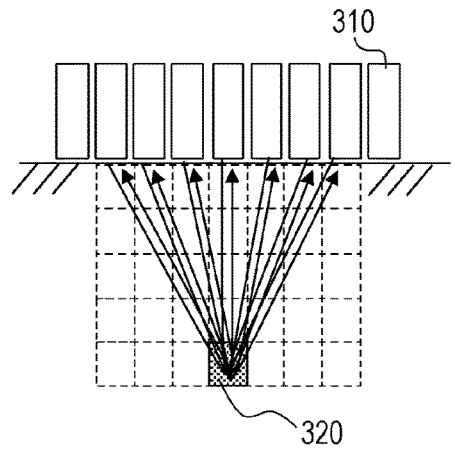

[Fig. 3B]
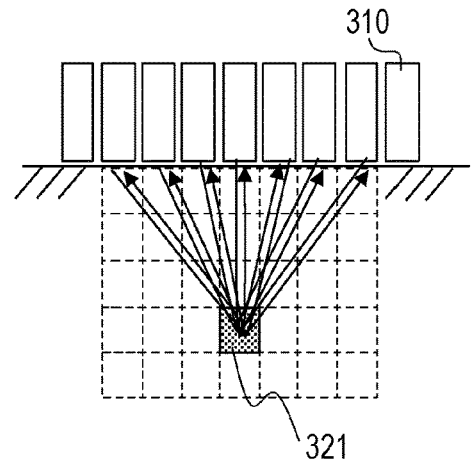
[Fig. 3C]
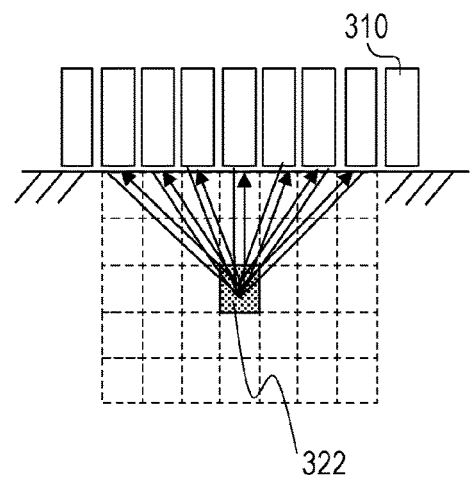
[Fig. 3D]
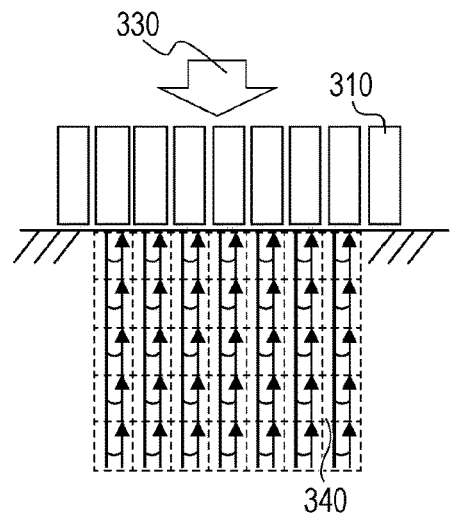

[Fig. 3E]
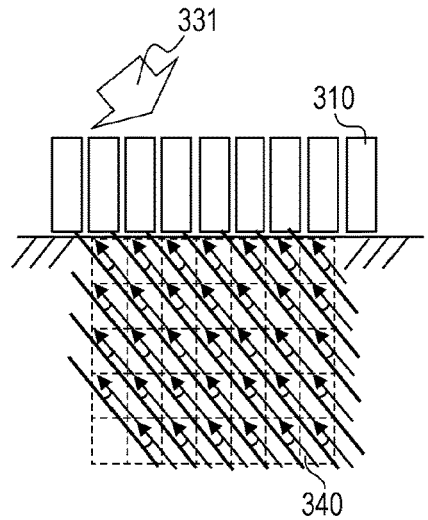
[Fig. 3F]
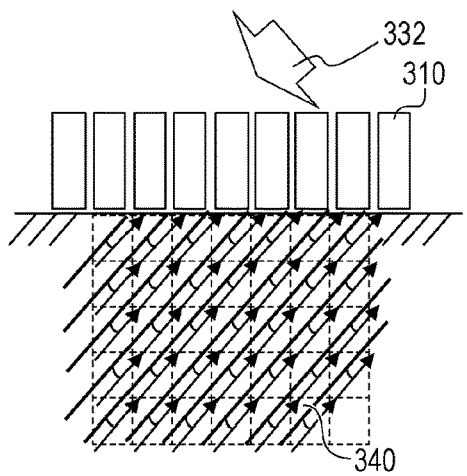
[Fig. 4A]
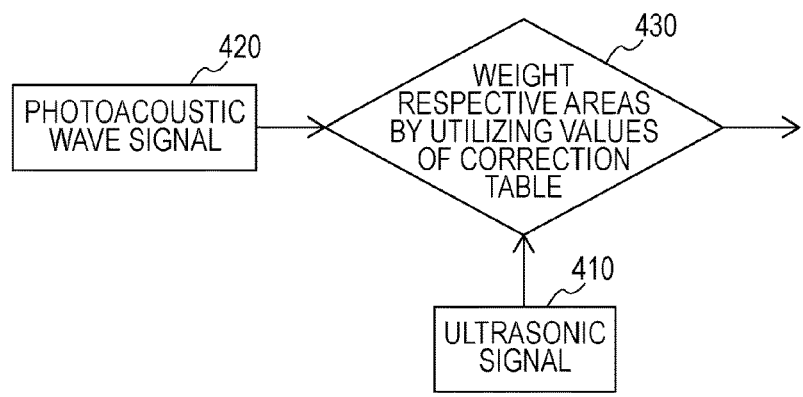

[Fig. 4B]
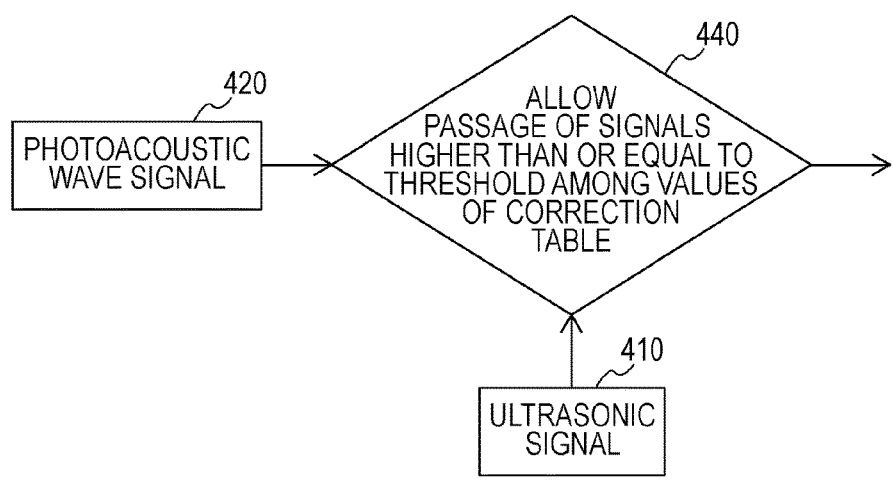

[Fig. 4C]
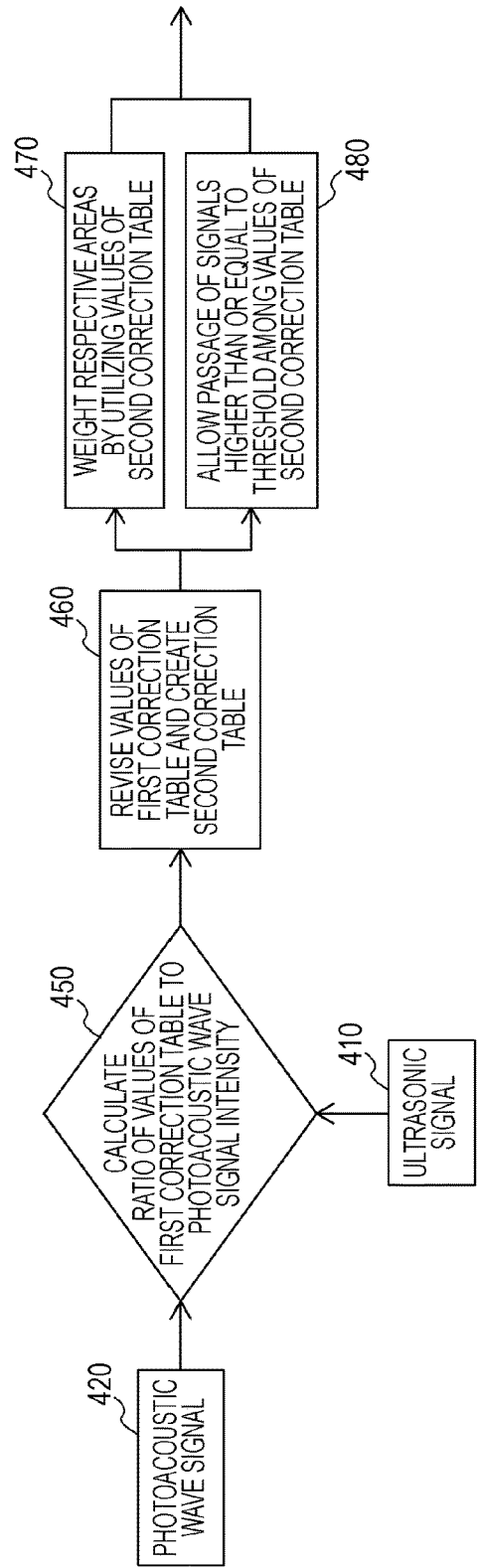

[Fig. 5A]
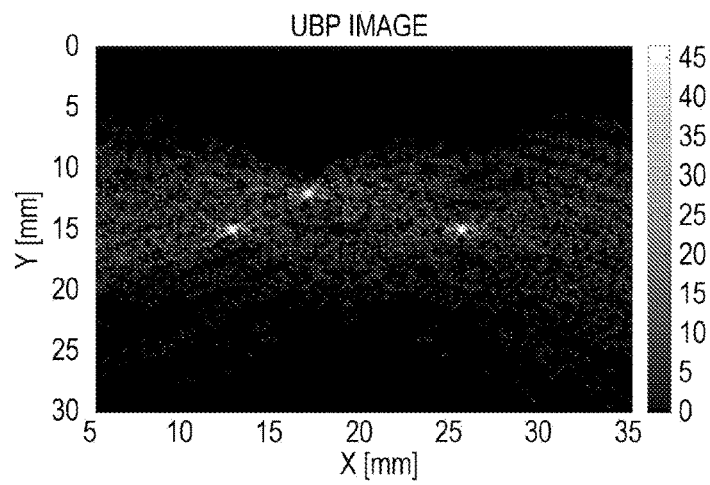
[Fig. 5B]
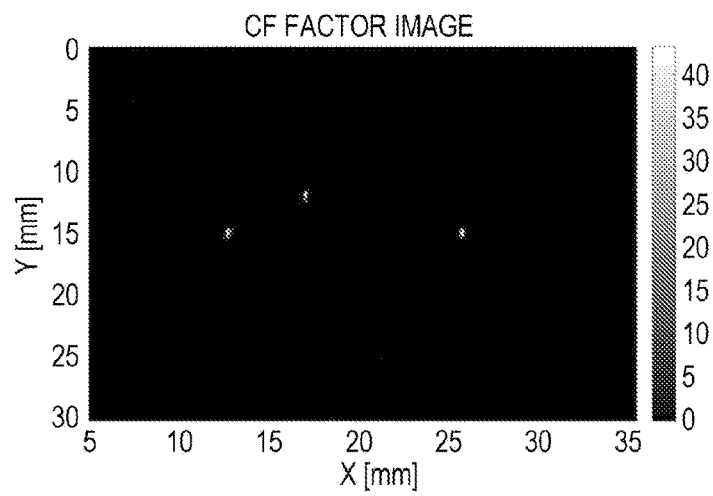
[Fig. 5C]
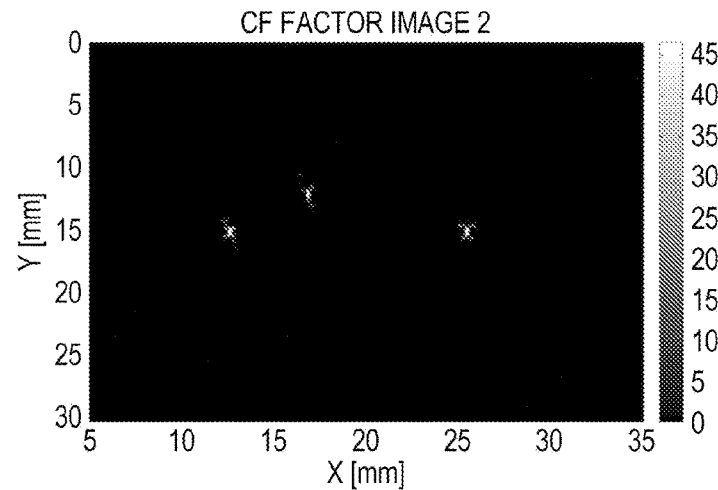

[Fig. 5D]
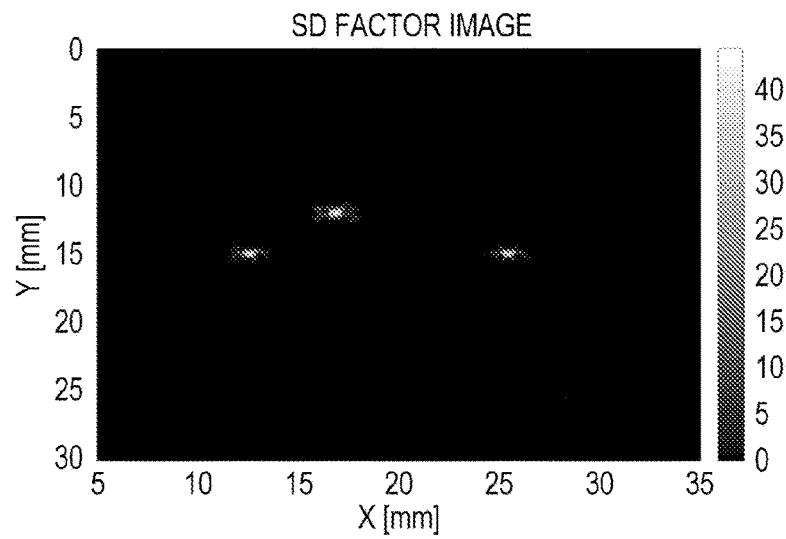
[Fig. 6A]
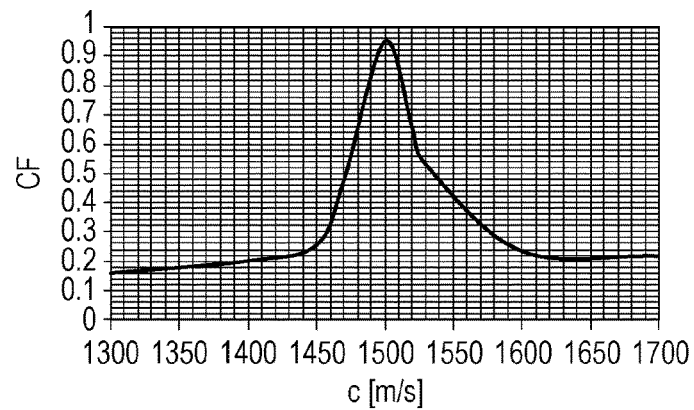
[Fig. 6B]
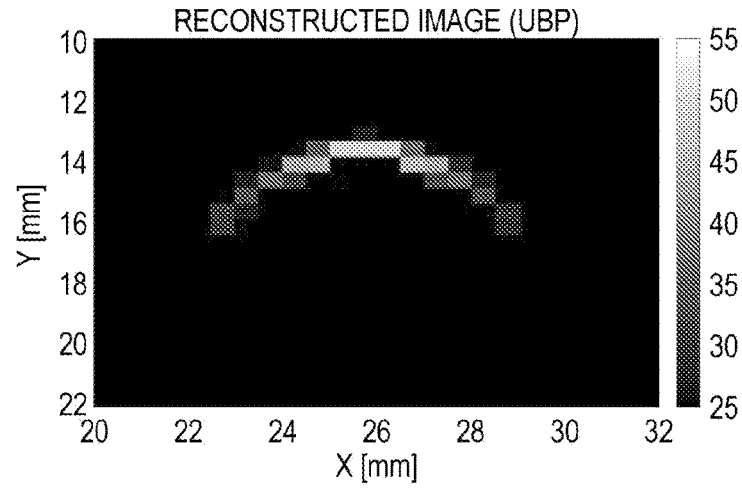

[Fig. 6C]
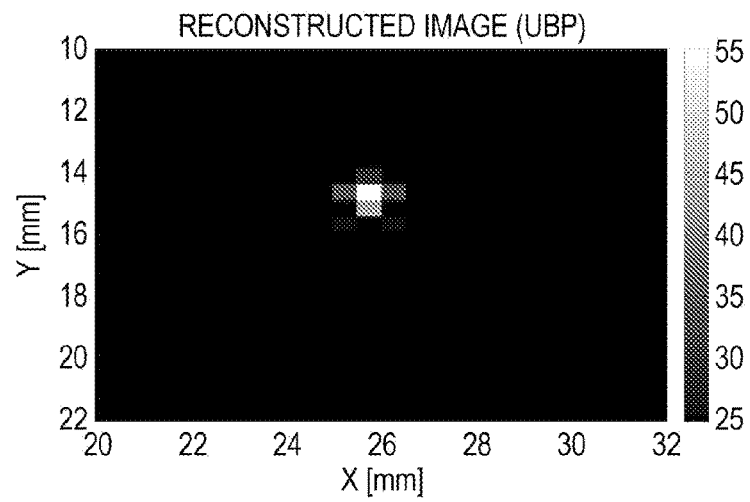
[Fig. 7A]
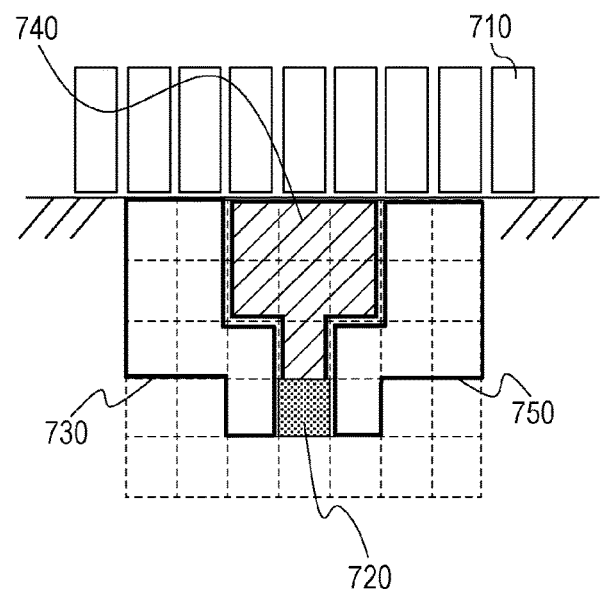

[Fig. 7B]
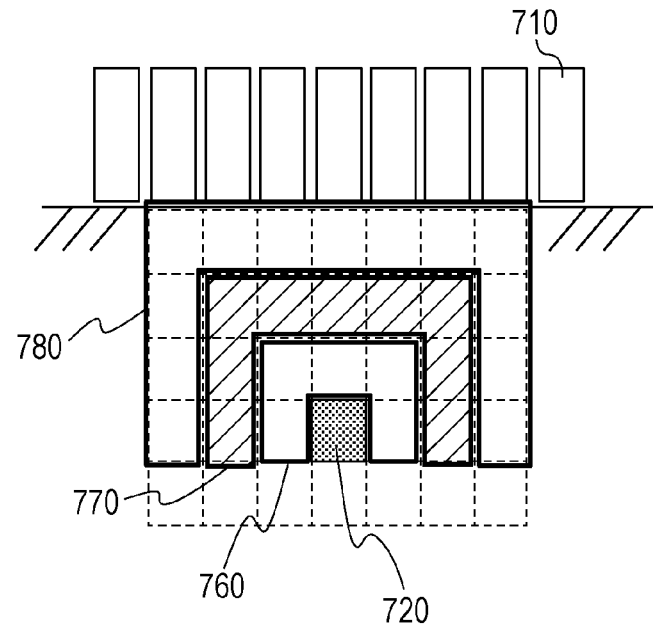
[Fig. 8]
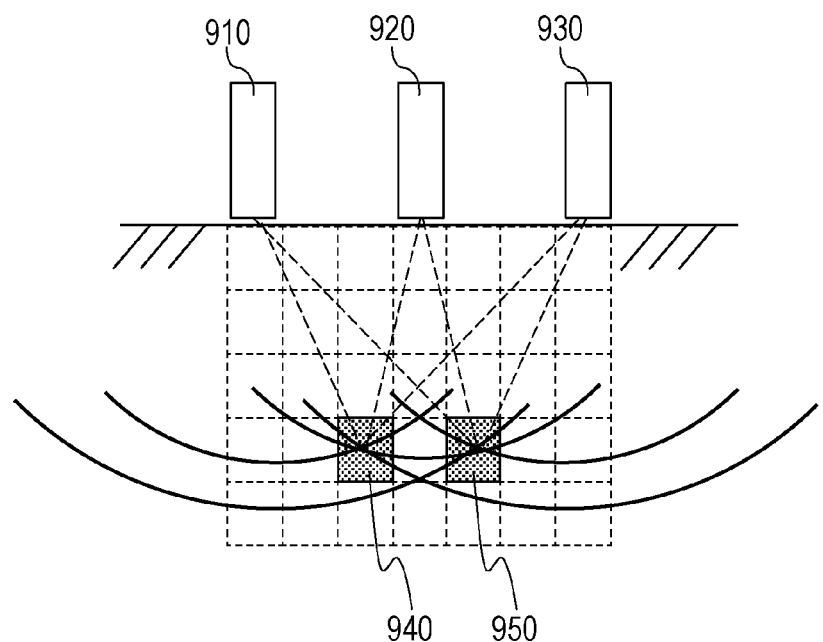

[Fig. 9]
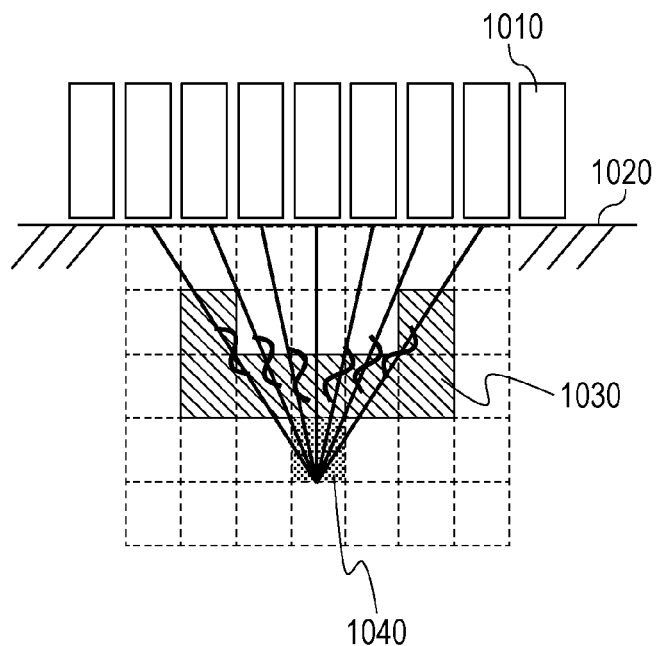

SUBJECT INFORMATION OBTAINING APPARATUS AND SUBJECT INFORMATION OBTAINING METHOD

TECHNICAL FIELD

The present invention relates to a subject information obtaining apparatus that obtains an optical characteristic value distribution of a subject by using a photoacoustic wave and a subject information obtaining method.

BACKGROUND ART

A research of a photo imaging technology for irradiating a living body with light from a light source such as a laser and imaging information of an internal body obtained on the basis of the incident light is advanced in a medical field. As one of the photo imaging technologies, Photo Acoustic Imaging (PAI) is proposed. In the photo acoustic imaging, a living body is irradiated with pulsed light generated from a light source. An acoustic wave (typically, an ultrasonic wave) generated from a body tissue that has absorbed energy of the pulsed light which is propagated and diffused in the living body is detected, and living body information is imaged on the basis of the detected signal.

That is, in the photo acoustic imaging, a difference in a rate of absorption for light energy between a subject part such as a tumor and other tissues is utilized, and an elastic wave (which is also referred to as photoacoustic wave) generated when the subject part absorbs the emitted light energy and instantaneously expands is detected by a photoacoustic wave detector (which is also referred to as transducer or probe). While this detection signal is subjected to an analysis process, it is possible to obtain an image of the optical characteristic value distribution.

In addition, by measuring these pieces of information with lights at various wavelengths, it is also possible to utilize the information in quantitative measurements for particular substances in the subject (for example, a concentration of hemoglobin included in blood, a degree of oxygen saturation of blood, and the like).

As described above, the subject is irradiated with the pulsed light in the photo acoustic imaging. The light is diffused in the subject because of a strong optical scattering characteristic, and photoacoustic waves are generated from a wide sphere at the same time. As a result, a resolution of the photoacoustic image is decreased.

In view of the above, to solve this problem, a technique of evaluating signals at generation locations of the photoacoustic waves detected by the respective photoacoustic wave detectors is adopted. According to this technique, with respect to the signals spreading in a concentric fashion, if the respective photoacoustic wave detectors can receive the same signal intensity, it is determined that the signal is a signal from an optical absorber. On the other hand, if the respective photoacoustic wave detectors do not receive the same signal intensity, it is determined that the signal is a noise signal. As an example of this technique, a factor called Coherence Factor (CF) is utilized according to NPL 1. The CF is a value calculated in the following expression for each area after data $$Si (1 \leq i \leq N) \quad [\text{Math.1}]$$

observed by each of N pieces of photoacoustic wave detectors is allocated to the respective areas through a back projection method such as Circular back projection.

[Math. 2]

$$CF = \frac{\left(\sum_{i=0}^{N-1} S_i\right)^2}{N \sum_{i=0}^{N-1} (S_i)^2} \quad (1)$$

According to the above-mentioned expression, in an area where the photoacoustic wave is generated, the CF is close to 1. In an area where the photoacoustic wave is not generated or an area where random noise is observed, the same signal intensity is not detected by the respective photoacoustic wave detectors, and the CF is close to 0. For that reason, since the CF becomes an index indicating a variation rate of the signals observed from the respective transducers for each area, it is possible to increase a reliability of the signals by weighting the respective signals with the CF as a coefficient. When the thus weighted signals are used, an improvement in the resolution can be realized for reconstructing the image, and it is also possible to decrease an influence of artifacts.

CITATION LIST

Non Patent Literature

NPL 1: C.-K. Liao, et al. "Optoacoustic imaging with synthetic aperture focusing and coherence weighting", OPTICS LETTERS/Vol. 29, No. 21/Nov. 1, 2004

SUMMARY OF INVENTION

Technical Problem

However, according to the technology described in NPL 1, a problem occurs that an accurate CF is not calculated with respect to the absorber arranged at a particular location.

That is, in a case where a tissue having a shape arranged at an equal distance from acoustic wave detectors exist, an intensity of a signal source is not accurately estimated, and the CF is not correctly calculated. A reason thereof will be described by using FIG. 8.

FIG. 8 illustrates an example in which a sound source of an acoustic wave generated when a subject is irradiated with light is identified through a back projection based on Circular back projection, and a signal variation is calculated.

In FIG. 8, three transducers 910, 920, and 930 are arranged as acoustic wave detectors on the subject, and on the basis of signals obtained from sound sources 940 and 950 at two locations, the locations of the sound sources 940 and 950 are identified. That is, if the photoacoustic waves at the same intensity are detected by the plural transducers, it is possible to estimate that those photoacoustic waves are generated from the same sound source, and by using a detection time from the light irradiation, the location of the sound source is identified.

At this time, a distance from the transducer 910 to the sound source 940 and a distance from the transducer 930 to the sound source 940 are different from each other, and a distance from the transducer 910 to the sound source 950 and a distance from the transducer 930 to the sound source 950 are also different from each other. For this reason, even when the photoacoustic waves at the same intensity are generated from the sound source 940 and the sound source 950, the transducer 910 and the transducer 930 can separate photoacoustic wave information from the sound source 940 and photoacoustic wave information from the sound source 950 from each other.

On the other hand, with regard to the transducer 920, since a distance from the transducer 920 to the sound source 940 and a distance from the transducer 920 to the sound source 950 are equal to each other, the transducer 920 receives the photoacoustic waves from the sound source 940 and the sound source 950 at the same time. For this reason, in a case where the photoacoustic waves at the same intensity are generated from the sound source 940 and the sound source 950, a signal intensity stronger than the signal intensity generated from the respective sound sources by two times is assigned to a circular arc including the sound source 940 and the sound source 950.

If the sound source 940 and the sound source 950 generate the equal signal intensity, both the CFs become 1, and it is expected that no variations of the signal intensity exist. However, as described above, in a case where the absorber is arranged at an equal distance from certain transducers, if the back projection technique is executed for identifying the signal source, an accurate estimation of the intensity of the signal source is not carried out. As a result, the CF is not suitable as the weighting factor, which may not contribute to the improvement in the resolution of the photoacoustic image.

In view of the above, the present invention provides a subject information obtaining apparatus and a subject information obtaining method with which the resolution of the photoacoustic image can be improved even when the absorber arranged at a particular position with respect to the detectors for the photoacoustic waves is used.

Solution to Problem

A subject information obtaining apparatus according to an aspect of the present invention includes: a light source configured to irradiate a subject with light; a photoacoustic wave detector configured to detect a photoacoustic wave generated in the subject on the basis of the light; an ultrasonic wave transmitter configured to transmit an ultrasonic wave to the subject; an ultrasonic wave detector configured to detect the ultrasonic wave that is transmitted from the ultrasonic wave transmitter and propagated within the subject; and a signal processing apparatus configured to obtain an optical characteristic value distribution of the subject, in which the signal processing apparatus executes generating a correction table on the basis of a variation quantity of a signal intensity related to a signal from the ultrasonic wave detector and processing a signal from the photoacoustic wave detector by using a value of the correction table.

Advantageous Effects of Invention

According to the aspect of the present invention, the subject information obtaining apparatus and the subject information obtaining method can be provided with which the resolution of the photoacoustic image can be improved even when the absorber arranged at a particular position with respect to the detectors for the photoacoustic waves is used.

BRIEF DESCRIPTION OF DRAWINGS

FIG. 1 is an explanatory diagram for describing a configuration of a subject information obtaining apparatus.

FIG. 2 is an explanatory diagram for describing a process flow.

FIG. 3A is an explanatory diagram for describing transmission and reception of ultrasonic waves.

FIG. 3B is an explanatory diagram for describing transmission and reception of ultrasonic waves.

FIG. 3C is an explanatory diagram for describing transmission and reception of ultrasonic waves.

FIG. 3D is an explanatory diagram for describing transmission and reception of ultrasonic waves.

FIG. 3E is an explanatory diagram for describing transmission and reception of ultrasonic waves.

FIG. 3F is an explanatory diagram for describing transmission and reception of ultrasonic waves.

FIG. 4A is an explanatory diagram for describing a manner of using a correction table.

FIG. 4B is an explanatory diagram for describing a manner of using the correction table.

FIG. 4C is an explanatory diagram for describing a manner of using the correction table.

FIG. 5A illustrates a calculation result described according to a first embodiment.

FIG. 5B illustrates a calculation result described according to the first embodiment.

FIG. 5C illustrates a calculation result described according to the first embodiment.

FIG. 5D illustrates a calculation result described according to a second embodiment.

FIG. 6A illustrates a calculation result described according to a third embodiment.

FIG. 6B illustrates a calculation result described according to the third embodiment.

FIG. 6C illustrates a calculation result described according to the third embodiment.

FIG. 7A illustrates a segmentation described according to the third embodiment.

FIG. 7B illustrates a segmentation described according to the third embodiment.

FIG. 8 is an explanatory diagram for describing a technical problem addressed by embodiments of the present invention.

FIG. 9 is an explanatory diagram for describing an image obtained in a case where a setting of a sound velocity is inappropriate.

DESCRIPTION OF EMBODIMENTS

As described above, if an attempt is made to identify the sound source of the photoacoustic wave signal through the back projection, the variation quantity of the signal intensity such as the CF is not correctly evaluation. In view of the above, according to the aspect of the present invention, the photoacoustic wave signal is corrected by utilizing the variation quantity of the signal intensity related to the ultrasonic wave signal. That is, when beam forming is used, the ultrasonic wave can be transmitted to a particular area, and the ultrasonic wave signal can be selectively received from the particular area. Thus, an estimation process for the signal source through the back projection which causes a problem in the photoacoustic wave signal is not carried out. For this reason, with respect to the variation quantity of the signal intensity too, as compared with the measurement technique based on the optical ultrasonic wave, a restriction such as a positional relationship between the respective transducers and the absorber is avoided. Therefore, according to the aspect of the present invention, it is possible to obtain the photoacoustic image having a high resolution.

FIG. 1 schematically illustrates a subject information obtaining apparatus. The subject information obtaining apparatus includes a laser generation apparatus 110, an optical apparatus 120, a probe 130, a control apparatus 140, a signal processing apparatus 150, and an image display apparatus 160.

The probe 130 is provided with a function of an ultrasonic wave transmitter that transmits an ultrasonic wave to a subject 100 and a function of an ultrasonic wave detector that detects the ultrasonic wave propagated within the subject 100.

Pulsed laser light 121 that is generated from the laser generation apparatus 110 functioning as a light source and emitted via the optical apparatus 120 to the subject 100 generates a photoacoustic wave 103 from an optical absorber 101. The probe 130 is also provided with a function of a photoacoustic wave detector that detects the photoacoustic wave 103. It is noted that the ultrasonic wave transmitter, the ultrasonic wave detector, and the photoacoustic wave detector may not be configured in an integrated manner and may be individually arranged.

The photoacoustic wave 103 detected by the probe 130 is subjected to an A/D conversion or the like by the control apparatus 140, and the signal processing apparatus 150 generates an optical characteristic value distribution of the subject 100. Herein, the optical characteristic value distribution is an initial sound pressure distribution, an optical absorption energy density distribution, an optical absorption coefficient distribution, or the like. Image data related to the optical characteristic value distribution output from the signal processing apparatus 150 is input to the image display apparatus 160, and the image is displayed on a display.

FIG. 2 illustrates a measurement flow carried out in the apparatus configuration of FIG. 1.

First, by using the probe 130, the ultrasonic wave is transmitted and received with a subject such as a living body (S1). The transmitted ultrasonic wave is reflected in a part having a large difference in an acoustic impedance within the subject to become an echo signal. The echo signal detected by the probe 130 is amplified by the control apparatus 140 to become A/D converted data.

Next, the signal processing apparatus 150 calculates the variation quantity of the signal intensity from the respective transducers with regard to the respective areas on the basis of the data obtained from the control apparatus 140 (S2).

Next, the signal processing apparatus 150 creates a correction table from the variation quantity of the signal intensity (S3).

It is noted that at this time, with regard to a predetermined area, an optimal sound velocity where the variation quantity of the signal intensity becomes small may be calculated (S4), and a sound velocity table may be created (S5).

Next, the photoacoustic wave 103 is generated from the optical absorber 101 by the laser light emitted from the laser generation apparatus 110, and the photoacoustic wave 103 is detected by the probe 130 (S6).

Next, in the signal processing apparatus 150, a correction is conducted on the photoacoustic wave signal on the basis of the correction table that is calculated through the obtainment of the ultrasonic wave signal, and a signal processing for imaging the photoacoustic wave signal (S7). It is noted that at this time, the correction may be conducted by utilizing the sound velocity table created in S5.

Finally, the image data is output from the signal processing apparatus 150 to the image display apparatus 160 (S8).

According to the above-mentioned configuration, since the correction table created by utilizing the signal of the photoacoustic wave can be corrected by using the ultrasonic wave signal, it is possible to obtain more appropriate image data of the optical characteristic value distribution.

It is noted that the ultrasonic wave generates the reflection wave on the basis of the difference in the acoustic impedance within the subject, and properties of the signals are different between the photoacoustic wave generated on the basis of the magnitude of the optical absorption coefficient within the subject and the ultrasonic wave. However, since the ultrasonic wave and the photoacoustic wave can obtain the signals with respect to the same area, information obtained by utilizing the ultrasonic wave can be used in the signal processing for the photoacoustic wave.

Hereinafter, respective steps illustrated in FIG. 2 will be described in more detail.

S1: Step of Transmitting and Receiving Ultrasonic Wave

To obtain the echo signals in the respective areas, transmission and reception of the ultrasonic wave after the beam forming are performed by the ultrasonic wave transmitter and the ultrasonic wave detector.

FIG. 3A, FIG. 3B, FIG. 3C, FIG. 3D, FIG. 3E, and FIG. 3F illustrate modes of the beam forming. As illustrated in FIG. 3A, by controlling phases of the respective transducers 310, a value of a focus area 320 can be obtained. By thus creating the focus area, the values of the respective areas on the basis of the one-time transmission wave can be obtained from the respective transducers. Also, as illustrated in FIG. 3B and FIG. 3C, in a case where a signal of another area is further obtained, the phase controls of the respective transducers 310 are changed, and the focus area can be moved to locations denoted by reference signs 321 and 322.

In addition, as illustrated in FIG. 3D, FIG. 3E, and FIG. 3F, while the phases of the respective transducers 310 are set to be uniform as plane waves, as denoted by reference sign 340, it is possible to obtain the information in a wide range. Furthermore, as indicated by reference signs 330, 331, and 332 in FIG. 3D, FIG. 3E, and FIG. 3F, it is also possible to appropriately change a direction of the transmitted ultrasonic wave.

As described above, in order to obtain the signals of the respective areas on the basis of the ultrasonic wave, the transmission and reception wave of the ultrasonic wave in accordance with the area scale for the measurement is preferably selected to obtain the signals.

S2: Step of Calculating Variation Quantity of Signal Intensity

On the basis of obtained the ultrasonic wave signal, a variation of the signal intensity in the respective areas is calculated. The amplified and A/D converted echo signals from the respective areas are subjected to a phasing addition on the basis of the sound velocity distribution within the subject, and a signal intensity Si for each area is calculated.

Next, as a first correction table, a variation quantity of the signal intensity Si is calculated. As an index of the variation quantity, a coherence factor (CF), a standard deviation (SD), or the like is used, but a variance, a difference from an average value, or the like may also be used as the variation quantity. In addition, the number of samples can also be appropriately changed.

For example, the standard deviation (SD) can be represented in the following expression while an average value of Si is set as $S_0$ and the number of probes that detect the signals from the respective areas is set as N.

[Math. 3]

$$SD = \sqrt{\frac{1}{N} \sum_{i=0}^{N-1} (S_i - S_0)^2} \quad (2)$$

S3: Step of Creating Correction Table

The variation value of the signal intensity calculated for each area in S2 is stored in a memory or the like as a correction table (first correction table).

Also, with regard to the numeral values of this first correction table, a table in which a proportion is changed may be newly created (second correction table). In addition, a ratio of the signal quantities of the photoacoustic waves is calculated, and with respect to areas indicating a proportion higher than or equal to a certain threshold, a value obtained by subtracting the numeric value on the first correction table may be set as the second correction table.

In a case where the proportion is changed, the numeric value for the correction is defined between 0 and 1, and therefore a maximum value or a value pursuant to this maximum value may be used. A 0 point may be defined as a minimum value or a value pursuant to this minimum value, but in a case where the signal of the photoacoustic wave which will be described below is dealt with, an average system noise intensity or a value pursuant to this intensity may be defined as 0.

It is noted that in the present application, since the second correction table is created on the basis of the first correction table, the second correction table may also be represented as the correction table that is created on the basis of the variation quantity of the signal intensity in some cases.

S4: Step of Deciding Optimal Sound Velocity

Next, optimal acoustic velocities in the respective areas are calculated from the obtained ultrasonic wave signal.

When the pieces of data obtained from the respective transducers are subjected to back projection to the respective areas, the image may be reconstructed while the sound velocity components in the subject are uniformly set, for example, as 1540 m/s. However, the actual sound velocity in the subject may vary from this set value, or an appropriate sound velocity may vary for each area of the subject in some cases. For that reason, as illustrated in FIG. 9, in a case where a sound velocity from a subject 1020 is detected by the respective transducers 1010 and the respective signals are subjected to back projection to an area 1040, if an area where the sound velocity varies exists, the respective signals are shifted. As a result, since an image is formed also in an area 1030 that is shifted from the area 1040, this area becomes a blurred area, and the resolution is deteriorated. In view of the above, by utilizing the variation quantity of the signal intensity calculated in S2 described above, if this sound velocity shift is set as an optimal value, it is possible to obtain an image without the blur where the resolution is improved.

Initial sound velocity values in the respective areas are stored in the memory or the like as the table. For example, if the subject is a living body, 1540 m/s that is an average sound velocity of a soft tissue or the like is substituted. This initial value can be appropriately selected in accordance with a situation of the subject body from a range between 1450 m/s of fat to 1580 m/s of bone or the like. Next, the sound velocity value is changed, for example, from 1450 m/s to approximately 1580 m/s, the calculation of the variations in the respective areas in the correction table is repeatedly carried out, and the sound velocity value where the variation becomes small is set as the optimal sound velocity value. The optimal sound velocity value may be obtained by utilizing a least-square method or other convergence test methods.

S5: Step of Creating Sound Velocity Table

The optimal sound velocity value calculated in the process in S4 described above is stored in the memory as a sound velocity table. Also, the variation value may be calculated again on the basis of the above-mentioned sound velocity table to create the correction table. It is noted that as described above, the process in S4 and the process in S5 may be omitted.

S6: Step of Detecting Photoacoustic Wave by Emitting Light

Light is emitted from a light source, and a photoacoustic wave is detected by the photoacoustic wave detector.

For the light source, a pulsed light source that can generate pulsed light in the order from several nanoseconds to several hundreds of nanoseconds is desirably used. To be more specific, to efficiently generate the photoacoustic waves, a pulse width of approximately 10 nanoseconds is used. For the light source, a light emitting diode or the like can also be used instead of the laser. For the laser, various lasers such as a solid-state laser, a gas laser, a dye laser, and a semiconductor laser can be used. For a wavelength of the light source to be used, a wavelength at which the light is propagated to the inside of the subject is desirably used. To be more specific, in a case where the subject is a living body, a wavelength higher than or equal to 500 nm and lower than or equal to 1200 nm is desirably used.

The photoacoustic wave detector is configured to detect an acoustic wave to be converted into an electric signal that is an analog signal. Any detector may be used so long as the detector can detect an acoustic wave signal such as the detector using a piezoelectric phenomenon, an optical resonant, a change in an electrostatic capacity, or the like. The photoacoustic wave detector may be separately provided from the ultrasonic wave detector, but when a signal detection in the same area, a space saving, and the like are taken into account, the detection is desirably conducted by the same detector.

S7: Step of Correcting Photoacoustic Wave Signal

A method of correcting the photoacoustic signal by utilizing the correction table will be described.

FIG. 4A and FIG. 4B illustrate a correction of the photoacoustic wave signal by utilizing the variation value of the signal intensity calculated on the basis of the ultrasonic wave signal as the correction table.

In FIG. 4A, the correction table is created from the ultrasonic wave signal 410, and a correction is executed on the photoacoustic wave signal 420 on the basis of the correction table. Herein, as denoted by reference sign 430, a weighting is conducted on the corresponding respective areas of the photoacoustic wave signal by multiplying the variation value of the signal intensity (for example, a value between 0 and 1 in the case of the CF) by the value of the photoacoustic signal.

In FIG. 4B, as denoted by reference sign 440, the following process is carried out. That is, an arbitrary threshold is decided with respect to the variation value of the signal intensity, and among the values of the correction table, signals higher than or equal to the threshold are not used for a computation process. The signals lower than the threshold are used for the computation process.

According to the technique described above in FIG. 4A, since the variation value of the signal intensity is multiplied by the signal of the photoacoustic wave, the quantitative property is lost. However, according to the technique described in FIG. 4B, since the quantitative property of the photoacoustic wave signal is not lost, the absorption coefficient or the like can be quantitatively calculated and also used for a functional imaging such as the degree of oxygen saturation.

It is noted that as described above, the correction table may be used before the image reconstruction and also may be used after the image reconstruction. Also, in this step, the process such as the image reconstruction may be carried out by utilizing the sound velocity table created in S5. In addition, the signals higher than or equal to the threshold are not used for the computation process in the above description, but the condition can be appropriately changed depending on a type of the variation quantity of the signal intensity.

FIG. 4C illustrates a method of changing the correction table.

According to this method, a correlativity between the variation value of the signal intensity obtained from the ultrasonic wave signal and the photoacoustic wave is digitalized. For example, in a case where the CF is used as the variation value of the signal intensity, since the CF is a value in a range from 0 to 1, by setting the photoacoustic signal as a value in a range from 0 to 1, a ratio of the value of the CF to the intensity of the photoacoustic signal is calculated with respect to the respective areas. At this time, in a case where the value of the CF is large and the photoacoustic wave signal is also large, the ratio thereof approaches 1.

On the other hand, a situation where the noise is adversely enhanced as a result of taking into account the value of the CF corresponds to a case in which the value of the CF is large and the photoacoustic wave signal is close to the system noise level. In this case, the ratio of the value of the CF to the intensity of the photoacoustic signal indicates a value in a range from 2 to 3, for example.

Therefore, in a case where this ratio exceeds the threshold, it is possible to determine that the relevant area is a noise component of the photoacoustic signal.

To be more specific, as denoted by reference sign 450 in FIG. 4C, a ratio of the values of the first correction table having the variation quantity of the ultrasonic wave signal intensity to the intensity of the photoacoustic wave signal is calculated.

Next, as denoted by reference sign 460, the second correction table is created by revising the values of the first correction table. For example, with regard to the area where the calculated ratio exceeds the threshold, a revision of subtracting the variation quantity of the signal intensity is conducted. It is noted that the example of the CF has been illustrated in the above description, but the threshold can be appropriately selected while taking into account the type of the variation quantity of the signal intensity.

Then, as denoted by reference signs 470 and 480, by using the revised values of the second correction table, the image reconstruction can be carried out by conducting a weighting correction on the signals of the respective areas, and the image reconstruction can be carried out after the signals higher than or equal to the threshold are passed through.

As a technique of the image reconstruction, an image reconstruction in a time domain format such as Circular back projection can be used.

It is noted that in the above, the description has been given in the order from Si to S8, but the order can be appropriately changed. For example, after the photoacoustic wave is detected, the correction table may be created. Also, these flows may appropriately enter a loop. For example, after the correction table is created, the sound velocity table is created, and furthermore, the correction table may be created again by utilizing this sound velocity table. In addition, a program for causing a computer to execute the above-mentioned steps is also included in the scope of the present invention.

First Embodiment

According to a first embodiment, a calculation result after the correction described in FIG. 4A and FIG. 4B is carried out while the CF is set as the correction table.

FIG. 5A illustrates a photoacoustic wave image where the image reconstruction is conducted on the basis of the signals of the photoacoustic waves generated from three points. At this time, the transducers configured to detect the photoacoustic wave are arranged at 256 locations, and the reconstruction is carried out on the basis of the photoacoustic wave signals detected by these transducers. In FIG. 5A, artifacts are confirmed in a radial pattern from the point where the sound source is arranged.

FIG. 5B illustrates a result after the weighting process illustrated in FIG. 4A is carried out while the CF created by using the ultrasonic wave is set in the correction table. By carrying out this weighting process, since the equal weighting amount is added with respect to the three points where the sound source is arranged, as compared with the image illustrated in FIG. 5A, an effect of improving a legibility is obtained.

In addition, FIG. 5C illustrates a result after the process illustrated in FIG. 4B is carried out while the CF created by using the ultrasonic wave is set in the correction table. At this time, the threshold for the CF is set as 0.5. By carrying out this process, the legibility is improved. It is noted that as described above, the process illustrated in FIG. 4B is a useful process method for the reason that the quantitative property of the data is not lost.

Second Embodiment

According to a second embodiment, a method using the standard deviation (SD) is illustrated. It is noted that a description of parts common to the first embodiment will be omitted.

FIG. 5D illustrates a result after the SD is calculated with respect to the respective areas, a value obtained by standardizing this SD value is used as the correction table, and the weighting process is conducted in FIG. 5A. By carrying out this process, the equal weighting amount is applied with respect to the photoacoustic wave for each area, and the data from the signal source is emphasized with regard to all the three signals. With this configuration, only the center component having the strong signal intensity is extracted, the decrease in the legibility by the artifacts is alleviated.

Third Embodiment

According to a third embodiment, a description will be given of an example in which the image reconstruction for the photoacoustic wave is conducted by obtaining the sound velocity value at which the CF becomes high.

According to the present embodiment, an acoustic wave advancing at 1500 m/s from a point sound source is formed, and the CF is calculated from the transducers at 256 locations arranged in a straight line manner. The correction table where the sound velocity is substituted to the above-mentioned CF is uniformly set in the area to be changed to a rate between 1300 and 1700 m/s, and the sound velocity at which the value of the CF becomes the highest is calculated.

FIG. 6A illustrates a fluctuation of the value of the CF with respect to the sound velocity. 1500 m/s at which the value of the CF indicates a local maximum value is matched with 1500 m/s that is the previously set sound velocity value.

FIG. 6B and FIG. 6C illustrate results after the image reconstruction of the signal from the point sound source is conducted while the sound velocity values are respectively set as 1700 m/s and 1500 m/s. FIG. 6C where the image reconstruction is conducted by using the sound velocity value at which the value of the CF indicates the local maximum value illustrates a calculation result in which the point sound source is more clearly reconstructed as compared with FIG. 6B. As described above, by using the present technique, even when the standard sound velocity is not determined in the measurement for the subject or the like, the optimal sound velocity value can be calculated on the basis of the value of the CF.

It is noted that the sound velocity may not be uniformly set with respective to the respective areas. For the setting, an arbitrary segmentation may be set in accordance with the absorber distribution.

For example, as illustrated in FIG. 7A, areas may be set by arbitrarily segmenting an area from a transducer 710 to a focus area 720 (areas 730, 740, and 750). Also, as illustrated in FIG. 7B, areas may be set by arbitrarily segmenting an area in accordance with a distance from the focus area 720 (areas 760, 770, and 780). The sound velocity is set in the respective areas or pursuant areas, and a repeated calculation is conducted with respect to the respective areas to increase the value of the CF, so that the optimal sound velocity can be calculated. With regard to the setting of these areas, a setting may also be carried out from a relationship between a targeted image quality and a calculation time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-113908, filed May 20, 2011, which is hereby incorporated by reference herein in its entirety.

REFERENCE SIGNS LIST

100 subject
101 optical absorber
102 ultrasonic wave
103 photoacoustic wave
110 laser generation apparatus
120 optical apparatus
130 probe
140 control apparatus
150 signal processing apparatus
160 image display apparatus

The invention claimed is:

1. A subject information obtaining apparatus, comprising:
a photoacoustic wave detector configured to detect a photoacoustic wave that is generated from a subject by irradiating the subject with light, and to convert the detected photoacoustic wave into a photoacoustic wave signal;
an ultrasonic wave transmitter configured to transmit an ultrasonic wave to a region in the subject;
an ultrasonic wave detector configured to receive at a plurality of reception positions thereof the ultrasonic wave that is transmitted from the ultrasonic wave transmitter reflected in the subject and propagated within the subject, and to output a plurality of ultrasonic wave signals corresponding to the plurality of reception positions; and
a signal processing unit configured to:
calculate a coherence factor, expressed by an equation (1), of intensities of signals corresponding to the ultrasonic wave reflected at the region in the subject determined, using sound velocity of the subject, from the plurality of ultrasonic wave signals:

$$CF = \frac{\left(\sum_{i=0}^{N-1} S_i\right)^2}{N \sum_{i=0}^{N-1} (S_i)^2} \quad (1)$$

where N is a number of the reception positions, and Si is a signal intensity of a signal corresponding to the ultrasonic wave reflected at a region in the subject at the $i^{th}$ reception position,
wherein the signal processing unit is configured to:
calculate the coherence factor repeatedly for a plurality of sound velocities in order to calculate a plurality of coherence factors, each of the plurality of coherence factors corresponding to each of the plurality of sound velocities,
calculate, from the plurality of sound velocities corresponding to the plurality of coherence factors, an optimal sound velocity corresponding to the coherence factor indicating a local maximum value in the plurality of coherence factors,
calculate an optical characteristic value at the region in the subject by performing an image reconstruction process using a signal corresponding to the photoacoustic wave generated from the region determined, using the optimal sound velocity, from the photoacoustic wave signal, and
weight the optical characteristic value at the region with the coherence factor indicating the local maximum value in the plurality of coherence factors.

2. The subject information obtaining apparatus according to claim 1, wherein the optical characteristic value is an initial sound pressure, an optical absorption energy density, or an optical absorption coefficient.

3. The subject information obtaining apparatus according to claim 1, wherein the signal processing unit is configured to:
weight the optical characteristic value at the region by multiplying the optical characteristic value at the region by the coherence factor indicating the local maximum value in the plurality of coherence factors.

4. The subject information obtaining apparatus according to claim 1,
wherein, in a case where the coherence factor indicates that the local maximum value in the plurality of coherence factors is lower than or equal to a threshold, the signal processing unit is configured to reduce the optical characteristic value at the region.

5. The subject information obtaining apparatus according to claim 1,
wherein the ultrasonic wave transmitter is configured to transmit the ultrasonic wave to a focus region as the region in the subject by performing transmitting beam forming, and
wherein the ultrasonic wave detector is configured to convert the ultrasonic wave that is transmitted from the ultrasonic wave transmitter and reflected at the focus region into the signals corresponding to the ultrasonic wave reflected at the region in the subject.

6. The subject information obtaining apparatus according to claim 1, wherein the ultrasonic wave detector has a plurality of transducers.

7. The subject information obtaining apparatus according to claim 1, wherein the signal processing unit is configured to calculate, from the plurality of sound velocities corresponding to the plurality of coherence factors, the optimal sound velocity corresponding to the coherence factor indicating the local maximum value in the plurality of coherence factors by utilizing a least-square method.

8. A subject information obtaining method, comprising:
calculate a coherence factor, expressed by an equation (1), of intensities of signals corresponding to the ultrasonic wave reflected at a region in a subject determined, using sound velocity of the subject, from a plurality of ultrasonic wave signals:

$$CF = \frac{\left(\sum_{i=0}^{N-1} S_i\right)^2}{N \sum_{i=0}^{N-1} (S_i)^2} \quad (1)$$

where N is a number of the reception positions, and Si is a signal intensity of a signal corresponding to the ultrasonic wave reflected at a region in the subject at the $i^{th}$ reception position;
calculate the coherence factor repeatedly for a plurality of sound velocities in order to calculate a plurality of coherence factors, each of the plurality of coherence factors, corresponding to each of the plurality of sound velocities;
calculate, from the plurality of sound velocities corresponding to the plurality of coherence factors, an optimal sound velocity corresponding to the coherence factor indicating a local maximum value in the plurality of coherence factors;
calculate an optical characteristic value at the region in the subject by performing an image reconstruction process using a signal corresponding to the photoacoustic wave generated from the region determined, using the optimal sound velocity, from the photoacoustic wave signal; and weight the optical characteristic value at the region with the coherence factor indicating the local maximum value in the plurality of coherence factors.

9. The subject information obtaining method according to claim 8, wherein the optical characteristic value is an initial sound pressure, an optical absorption energy density, or an optical absorption coefficient.

10. The subject information obtaining method according to claim 8, wherein the optical characteristic value at the region is weighted by multiplying the optical characteristic value at the region by the coherence factor indicating the local maximum value in the plurality of coherence factors.

11. The subject information obtaining method according to claim 8,
wherein, in a case where the coherence factor indicates that the local maximum value in the plurality of coherence factors is lower than or equal to a threshold, the optical characteristic value at the region is reduced.

12. The subject information obtaining method according to claim 8, wherein the optimal sound velocity corresponding to the coherence factor indicates that the local maximum value in the plurality of coherence factors is calculated from the plurality of sound velocities corresponding to the plurality of coherence factors by utilizing a least-square method.

13. The subject information obtaining method according to claim 8, further comprising:
transmitting the ultrasonic wave to a focus region as the region in the subject by performing transmitting beam forming, and
converting the ultrasonic wave that is transmitted and reflected at the focus region into the signals corresponding to the ultrasonic wave reflected at the region in the subject.

14. The subject information obtaining apparatus according to claim 1, wherein the signal processing unit is configured to perform a circular back projection as the image reconstruction process.

15. The subject information obtaining method according to claim 8, wherein a circular back projection as the image reconstruction process is performed.

* * * * *